US008795186B2

(12) United States Patent
Genc

(10) Patent No.: US 8,795,186 B2
(45) Date of Patent: Aug. 5, 2014

(54) SYSTEM, METHOD, AND COMPUTER SOFTWARE CODE FOR PREDICTING AN ACUTE HYPOTENSIVE EPISODE

(75) Inventor: Sahika Genc, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 1070 days.

(21) Appl. No.: 12/751,729

(22) Filed: Mar. 31, 2010

(65) Prior Publication Data

US 2011/0245631 A1    Oct. 6, 2011

(51) Int. Cl.
*A61B 5/021* (2006.01)
*A61B 5/024* (2006.01)

(52) U.S. Cl.
USPC .......................... 600/485; 600/483; 600/513

(58) Field of Classification Search
USPC ................................................ 600/481–507
See application file for complete search history.

(56) References Cited

U.S. PATENT DOCUMENTS

| 8,060,190 | B2* | 11/2011 | Sornmo et al. | 600/509 |
| 8,287,725 | B2* | 10/2012 | Sornmo et al. | 210/85 |
| 8,311,619 | B2* | 11/2012 | Sornmo et al. | 600/515 |
| 2010/0249617 | A1* | 9/2010 | Leung et al. | 600/495 |

OTHER PUBLICATIONS

Ghaffari et al. "Predicting Acute Hypotensive Episodes Based on HR Baroreflex Model Estimation." Cardiovasc Eng (2009) 9:161-164.*
Ghaffari et al. Detection of AHE via a Trained Adaptive Network-Based Fuzzy Interference System (ANFIS). Journal of Electrical and Electronics Engineering Research vol. 2(2), pp. 025-047, Mar. 2010.*
Ursino, Mauro. "Interaction between carotid baroregulation and the pulsating heart: a mathematical model." Am J Physiol Heart Circ Physiol 275:H1733-H1747, 1998.*
Chiarugi et al. "Predicting the Occurrence of Acute Hypotensive Episodes: The PhysioNet Challenge." Computers in Cardiology, Sep. 13-16, 2009, pp. 621-624.*
Langley et al. "Predicting Acute Hypotensive Episodes from Mean Arterial Pressure." Computers in Cardiology, Sep. 13-16, 2009, pp. 553-556.*

* cited by examiner

*Primary Examiner* — Navin Natnithithadha
*Assistant Examiner* — Meredith Weare
(74) *Attorney, Agent, or Firm* — Scott J. Asmus

(57) ABSTRACT

A system for determining onset of an acute hypotensive episode, the system includes a plurality of collectors configured to determine heart rate, mean arterial pressure, stroke volume, total peripheral resistance, and/or age of a patient, an estimate model configured to receive data from the collectors, a simulate model configured to receive information from the estimate model to simulate operation of an effector portion and a neural portion of an arterial baroreceptor reflex pathway, and a prediction model configured predict onset of an acute hypotensive episode based on results from the simulate model. A method and a computer software code for determining onset of an acute hypotensive episode are also disclosed.

12 Claims, 5 Drawing Sheets

SYSTEM, METHOD, AND COMPUTER SOFTWARE CODE FOR PREDICTING AN ACUTE HYPOTENSIVE EPISODE

BACKGROUND OF THE INVENTION

Exemplary embodiments of this invention relate generally to acute hypotensive episodes and, more particularly, to predicting an onset of an acute hypotensive episode in a patient.

An acute hypotensive episode (AHE) is a critical event that can lead to irreversible organ damage and death. AHE may be defined as any period of thirty (30) minutes or more during which at least ninety percent (90%) of Mean Arterial Pressure (MAP) measurements are at or below 60 mmHg. MAP is a term used in medicine to describe an average blood pressure in an individual. It is defined as the average arterial pressure during a single cardiac cycle.

AHE requires effective, prompt intervention. When detected in time, an appropriate intervention can significantly lower the risks for a patient. Determining what intervention is appropriate in any given case depend on diagnosing the cause of the episode, which might be sepsis, myocardial infarction, cardiac arrhythmia, pulmonary embolism, hemorrhage, dehydration, anaphylaxis, effects of medication, or any of a wide variety of other causes of hypovolemia, insufficient cardiac output, or vasodilatory shock.

To further illustrate how deadly AHE may be, a statistical study conducted on a database known as Multiparameter Intelligent Monitoring in Intensive Care-II (MIMIC-II), which encompasses a diverse and very large population of ICU patients, and contains high temporal resolution data including laboratory results, electronic documentation, and bedside monitor trends and waveforms. The database can support a diverse range of analytic studies spanning epidemiology, clinical decision-rule improvement, and electronic tool development. In this database, as of October 2008, five hundred and eleven (511) patients out of one thousand two hundred and thirty-seven (1,237) experiences AHE during a stay in an intensive care unit (ICU). The mortality rate for the 511 patients is more than twice that of the MIMIC-II population as a whole. Hospitals and patients would benefit greatly from being able to predict one or more occurrences of AHE prior to their onset.

BRIEF DESCRIPTION OF THE INVENTION

Embodiments of the present invention relate to a method, system, and computer software code for predicting (or determining) one or more occurrences of acute hypotensive episodes (AHE) prior to their onset. A method comprises reading heart rate data from a patient over a given time period, reading mean arterial pressure data from the patient over the given time period, and conditioning the heart rate data and the mean arterial pressure data for use in determining an onset of an acute hypotensive episode. The method further comprises calculating a mean and standard deviation of random coefficients of a specific order linear neural model with a maximum likelihood estimator based on past read heart rate and mean arterial pressure data of the patient, and generating predicted data points with mathematical models of a neural portion and an effector portion of a closed-loop system functioning of heart, vessels, and medullary cardiovascular centers with the calculated mean and standard deviation to determine the onset of the acute hypotensive episode. The method further comprises determining whether an acute hypotensive episode is occurring within the prediction window, and reporting the acute hypotensive episode and its onset time when detected.

Another exemplary method comprises determining heart rate and mean arterial pressure of a patient at a given time, and estimating an onset of an acute hypotensive episode based on the measured heart rate and mean arterial pressure at the given time in association with heart rate and mean arterial pressure time-series data prior to the given time within a predetermined period. The method further comprises simulating an evolution of mean arterial pressure based on a mathematical model of a neural portion for a predetermined prediction period and further based on a number of repetitive runs wherein the neural portion parameters are random coefficients of a linear system described as an nth order differential equation with random coefficients calculated via a maximum likelihood estimator using past read heart rate and mean arterial pressure of the patient over a predetermined estimation period, and predicting the acute hypotensive episode based on results from simulating the onset of the acute hypotensive episode.

The system comprises a plurality of collectors configured to determine heart rate, mean arterial pressure, stroke volume, total peripheral resistance, and/or age of a patient, and an estimate model configured to receive data from the collectors. The system further comprises a simulate model configured to receive information from the estimate model to simulate operation of an effector portion and a neural portion of an arterial baroreceptor reflex pathway, and a prediction model configured predict onset of an acute hypotensive episode based on results from the simulate model.

The computer software code is stored on a computer readable medium and configured for execution with a processor designated for collecting and controlling sharing of data associated with a patient's medical condition. The computer software code comprises a computer software module determining heart rate and mean arterial pressure of a patient at a given time, operable with the processor, and a computer software module for estimating an onset of an acute hypotensive episode based on the measured heart rate and mean arterial pressure at the given time in association with heart rate and mean arterial pressure time-series data prior to the given time within a predetermined period, operable with the processor. The computer software code further comprises a computer software module for simulating an evolution of mean arterial pressure based on a mathematical model of a neural portion for a predetermined prediction period and further based on a number of repetitive runs wherein the neural portion parameters are random coefficients of a linear system described as an nth order differential equation with random coefficients calculated via a maximum likelihood estimator using past read heart rate and mean arterial pressure of the patient over a predetermined estimation period. The computer software code also comprises a computer software module for predicting the acute hypotensive episode based on results from simulating the onset of the acute hypotensive episode, operable with the processor.

Another exemplary computer software code a computer software module for reading heart rate data from a patient over a given time period, operable with the processor, a computer software module for reading mean arterial pressure data from the patient over the given time period, operable with the processor, a computer software module for conditioning the heart rate data and the mean arterial pressure data for use in determining an onset of an acute hypotensive episode, operable with the processor. The computer software code further comprises a computer software module for calculating a mean and standard deviation of random coefficients of a specific order linear neural model with a maximum likelihood estimator based on past read heart rate and mean arterial pressure data of the patient, operable with the processor, and a computer software module for generating predicted data points with mathematical models of a neural portion and an effector portion of a closed-loop system functioning of heart, vessels, and medullary cardiovascular centers with the calculated mean and standard deviation to determine the onset of the acute hypotensive episode. The computer software module further comprises a computer software module for determining whether an acute hypotensive episode is occurring within the prediction window, operable with the processor, and a computer software module for reporting the acute hypotensive episode and its onset time when detected, operable with the processor.

BRIEF DESCRIPTION OF THE DRAWINGS

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the embodiments of the invention will be described and explained with additional specificity and detail through the use of the accompanying drawings in which.

DETAILED DESCRIPTION OF THE INVENTION

Figure 1:
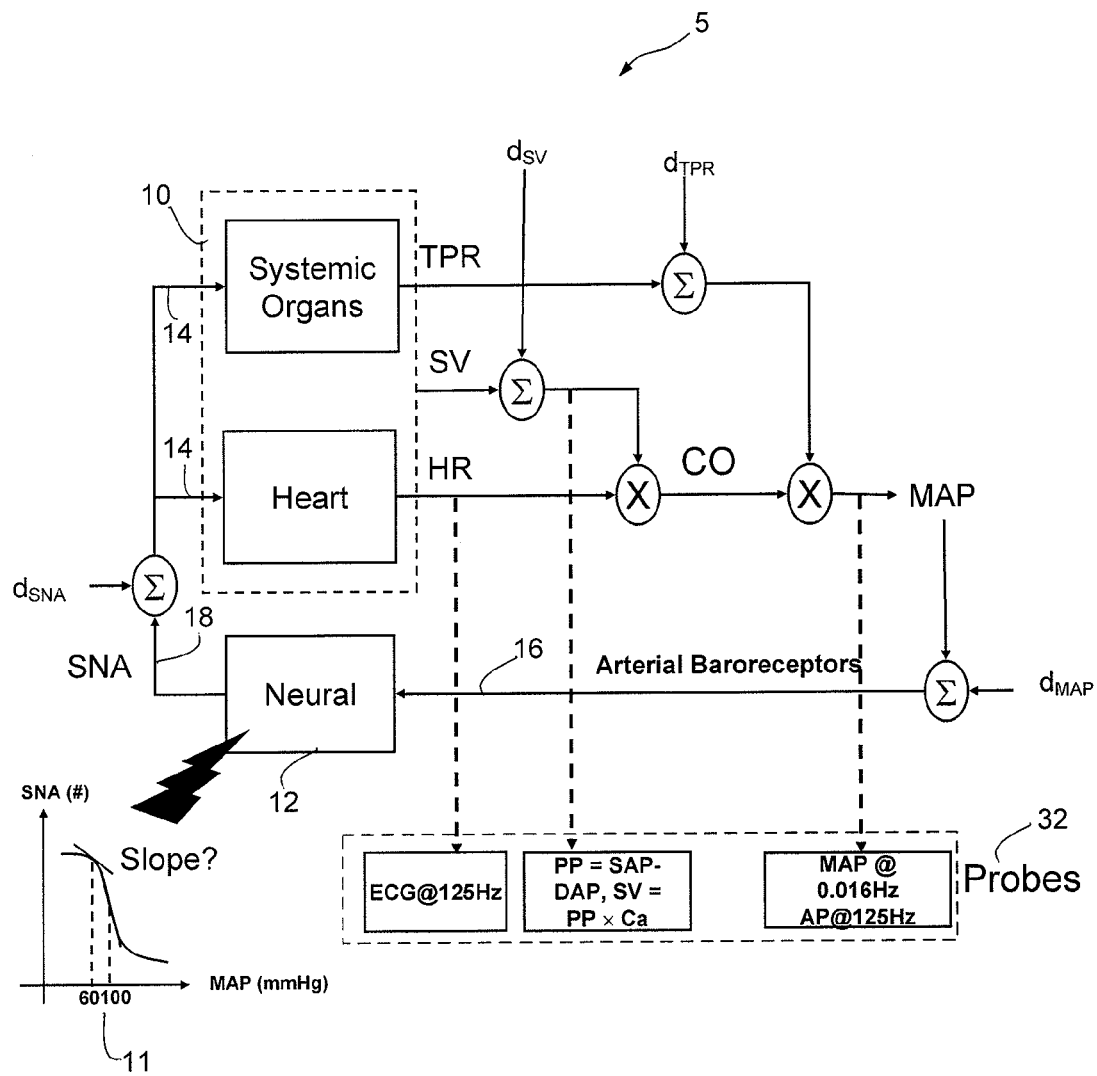
FIG. 1 depicts an exemplary embodiment of a mean arterial pressure regulation block diagram.

Reference will be made below in detail to exemplary embodiments of the invention, examples of which are illustrated in the accompanying drawings. Wherever possible, the same reference numerals used throughout the drawings refer to the same or like parts. As disclosed below, multiple versions of a same element may be disclosed. Likewise, with respect to other elements, a singular version is disclosed. Neither multiple versions disclosed nor a singular version disclosed shall be considered limiting. Specifically, although multiple versions are disclosed, a singular version may be utilized. Likewise, where a singular version is disclosed, multiple versions may be utilized.

Exemplary embodiments of the invention solve problems in the art by providing a system, method, and computer implemented method, such as a computer software code or computer readable media, for providing for determining onset of an acute hypotensive episode.

Persons skilled in the art will recognize that an apparatus, such as a data processing system, including a CPU, memory, I/O, program storage, a connecting bus, and other appropriate components, could be programmed or otherwise designed to facilitate the practice of the method of the invention. Such a system would include appropriate program means for executing the method of the invention.

Also, an article of manufacture, such as a pre-recorded disk, computer readable media, or other similar computer program product, for use with a data processing system, could include a storage medium and program means recorded thereon for directing the data processing system to facilitate the practice of the method of the invention. Such apparatus and articles of manufacture also fall within the spirit and scope of the exemplary embodiments of the invention.

Broadly speaking, a technical effect is to determine or predict an abnormal condition associated with a heart, such as but not limited to an onset of an acute hypotensive episode either prior to or as soon as onset begins. To facilitate an understanding of the exemplary embodiments of the invention, it is described hereinafter with reference to specific implementations thereof. Exemplary embodiments of the invention may be described in the general context of computer-executable instructions, such as program modules, being executed by any device, such as but not limited to a computer, designed to accept data, perform prescribed mathematical and/or logical operations usually at high speed, where results of such operations may or may not be displayed. Generally, program modules include routines, programs, objects, components, data structures, etc., that perform particular tasks or implement particular abstract data types. For example, the software programs that underlie exemplary embodiments of the invention can be coded in different programming languages, for use with different devices, or platforms. It will be appreciated, however, that the principles that underlie exemplary embodiments of the invention can be implemented with other types of computer software technologies as well.

Moreover, those skilled in the art will appreciate that exemplary embodiments of the invention may be practiced with other computer system configurations, multiprocessor systems, microprocessor-based or programmable medical electronics, minicomputers, mainframe computers, and the like. Exemplary embodiments of the invention may also be practiced in distributed computing environments where tasks are performed by remote processing devices that are linked through at least one communications network. In a distributed computing environment, program modules may be located in both local and remote computer storage media including memory storage devices.

Referring now to the drawings, embodiments of the present invention will be described. Exemplary embodiments of the invention can be implemented in numerous ways, including as a system (including a computer processing system), a method (including a computerized method), an apparatus, a computer readable medium, a computer program product, or a data structure tangibly fixed in a computer readable memory. Several embodiments of the invention are discussed below.

Though exemplary embodiments of the present invention are described with respect to Acute Hypotensive Episodes (AHE), exemplary embodiments of the invention are also applicable to other conditions described as a pattern in MAP similar to AHE that may be life threatening to patients. Towards this end, when discussing predicting an onset, this may include a task or requirement to be performed with respect to other life threatening medical conditions involving the heart.

FIG. 1 depicts an exemplary embodiment of a mean arterial blood pressure (MAP) regulation block diagram. The functioning of systemic organs and heart can be described by fluid dynamics. Exemplary embodiments of the invention disclosed herein are based on a model-based approach where a closed-loop system 5 functioning of the heart, vessels, and medullary cardiovascular centers (MCC), where short-term regulation of the mean arterial blood pressure (MAP) is considered. The MCC is a primary integrating center for baroreceptor reflexes in the brainstem medulla oblongata. When arterial baroreceptors decrease their discharge as a result of less MAP, sympathetic and parasympathetic nerve activity increases and decreases, respectively, that results in increasing heart rate, ventricular contractility, and vasoconstriction which elicits an increased secretion of Angiotensin II and vasopressin, which constrict arterioles. The heart and vessels form an effector portion 10 of an arterial baroreceptor reflex pathway and the MCC forms a neural portion 12 of the arterial baroreceptor reflex pathway. For the neural portion 12, what is known is how it reacts, i.e., when MAP increases SNA decreases, as illustrated in graph 11. Thus, the exact slope of a linear relation between MAP and SNA, regulated by medullary cardiovascular centers.

The input 14 to the effector portion 10 is the sympathetic nerve activity (SNA) and the parasympathetic nerve activity (PNA). The eventual output of the effector portion 10 is the MAP, which is also an input 16 to the neural portion 12. The MAP is not a direct output, but is a combination of the volume of blood ejected per minute from the heart or stroke volume (SV), heart rate (HR) and total peripheral resistance (TPR). As illustrated, the stroke volume (SV), which is output from the effector portion 10, is multiplied with the heart rate (HR), also outputted from the effector portion 10 to determine a cardiac output (CO). The CO is multiplied with a value from the total peripheral resistance (TPR), also output from the effector portion 10 to achieve the MAP. The output 18 of the neural portion 12 is the SNA/PNA (for simplicity of FIG. 1, only SNA is represented though PNA is also used), and is input to the effector portion 10, hence, the closed-loop system 5. Exemplary embodiments of the invention consider a built-in physics-based model that describes how MAP changes with respect to heart rate, stroke volume, and total peripheral resistance which is used to model the effector (heart and vessels) portion 10 of the closed-loop system 5. A disturbance may be added to each respective variable, specifically, $d_{SNA}$ is added to the SNA prior to input to the effector portion, $d_{SV}$ is added to the SV value prior to multiplying it with the HR to determine the CO, and $d_{TPR}$ is added to the TPR value prior to multiplying it to the CO to result in the MAP. A disturbance may be added to MAP specifically $d_{MAP}$ is added to the MAP prior to Neural 16. The effect of each disturbance, d, is negative. For example, suppose a certain amount of SNA, X, is needed to increase HR by a specific value, Y. If there were a disturbance to the SNA with an amount Z, such as neuro-shock, then when neural part wants to supply X to increase heart rate by Y it actually increases heart rate by Y-Z.

As explained in further detail below, the built-in effector portion 10 is integrated with the neural portion 12, which is built on-the-fly based on the vital signs data observed within a pre-specified learning period. Exemplary embodiments of the invention consider a linear differential equation model of the neural portion 12 with random coefficients. During the learning period, a maximum likelihood estimator is used to calculate the mean and standard deviation of the random coefficients of the neural portion 12 that are then used to generate random coefficients to predict the MAP in simulate model 35, output of the effector part, for a pre-specified prediction window. A probabilistic measure on occurrence of AHE in a prediction window is generated. If the probability is above a pre-specified value then the occurrence of the AHE is predicted and the onset time is output.

Figure 2:
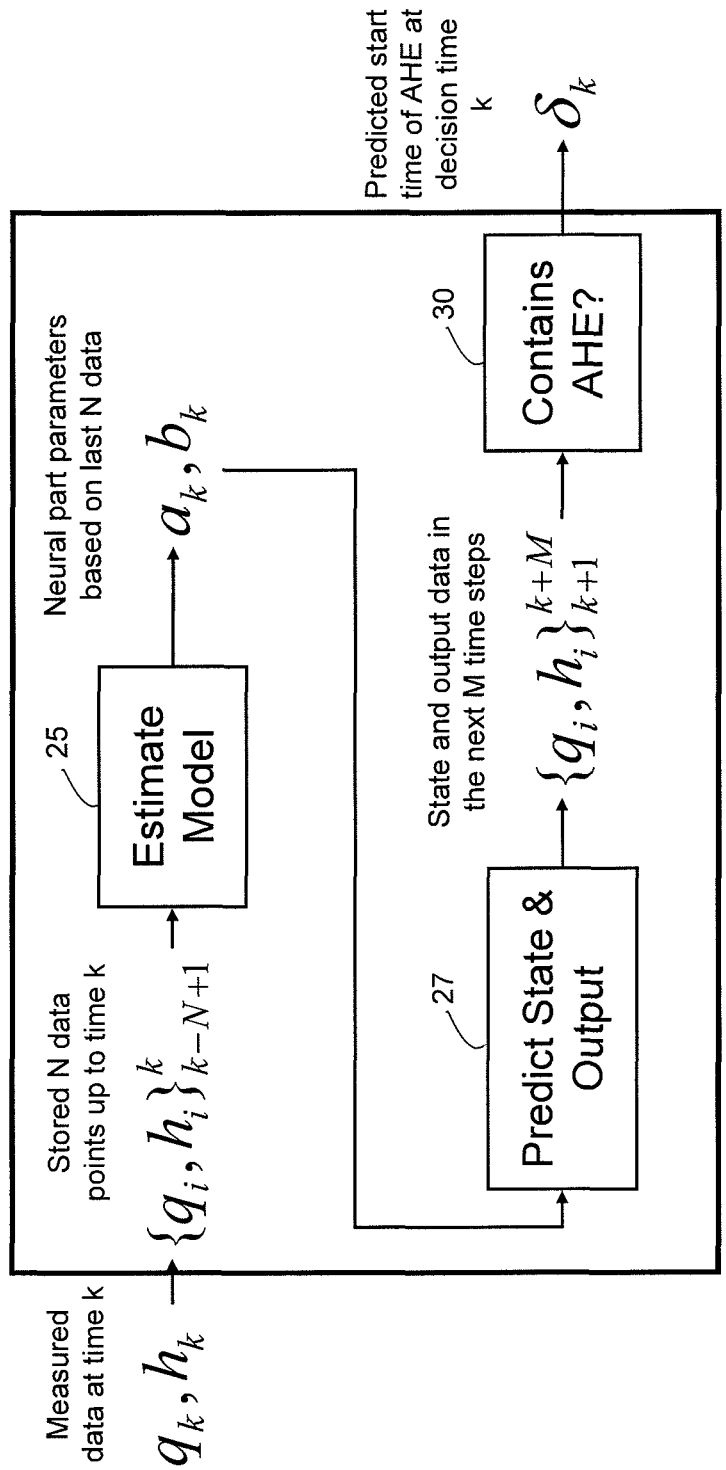
FIG. 2 depicts an exemplary embodiment of a predictive assessment algorithm block diagram.

FIG. 2 depicts an exemplary embodiment of a predictive assessment algorithm block diagram. An overall approach is to estimate parameters for the neural portion 12 and then integrate those parameters into the overall system 5 disclosed in FIG. 1 to predict a next set of values for MAP over a period of time. q corresponds to MAP, h to heart rate, N to an estimation window size, and M to a prediction window size. Measured MAP and heart rate data at a specific time, k, is provided along with stored data for an estimation window size, N, up to the specific time, k, to an estimate model 25. A goal of the estimate model 25 is to determine an exact model which implicitly calculates the unknown slope of graph 11. It is assumed that the neural portion 12 is a linear system described by differential equations with Gaussian random coefficients. It is considered that the random coefficients represent the lumped effect of underlying cell or molecular level activities that result in changes in the heart rate via changes in SNA and PNA. If variations in the random coefficients are observable, or measurable, they may be incorporated into the model. However, when they cannot be, they may be considered as random variables with specific characteristics such as having Gaussian probability distribution function. Thus, a model must be representative enough to derive suitable estimators for predicting an evolution of the system based on past read MAP and HR data over a pre-determined period for a patient, such as but not limited to thirty minutes. For example, the model for the neural portion may include the following formula:

$$h(t)=(a_1+\alpha_1)h(t-1)+\ldots+(a_n+\alpha_n)h(t-n)+\ldots+(b_1+\beta_1)q(t-1)+\ldots+(b_n+\beta_n)q(t-n);$$

where h(t) denotes heart rate and is the output of the neural portion 12, and q(t) denotes mean arterial pressure (MAP) and is the input to the neural portion 12, $a_1 \ldots a_n$ and $b_1 \ldots b_n$ are real coefficient, $\alpha_1 \ldots \alpha_n$ and $\beta_1 \ldots \beta_n$ are mutually independent Gaussian white noise with variance r>0, the input is independent of the random coefficients, and n is the order of the system. Then, the neural portion 12 parameters based on the last N data may be provided to an estimate state and output model 27, where a set of observations of input and output may be provided, such as:

$$\xi=\{h(1)\ldots h(N), q(1), \ldots, q(N-1)\}$$

estimate the vector of unknown parameters:

$$\phi^T=(a_1 \ldots a_n \ldots b_1 \ldots b_n r)$$

with respect to a cost function that maximizes the likelihood function. A conditional maximum likelihood estimator method may be applied as follows:

$$\phi=\arg[\max\_p(H_1|H_0,Q)]$$

where $H_1=\{h(n+1)\ldots h(n+N)\}$, $H_0=\{h(1)\ldots h(n)\}$ (initial state of the system), and $Q=\{q(1)\ldots q(N-1)\}$. The joint probability density P ($H_1|H_0$, Q) is expressed as a likelihood function of unknown parameters to be estimated and may be expressed as $$L(\phi)=\Pi^N_{t=n+1}p_t(h(t)|z(t-1))$$

where $p_t$ is the probability density function of the random variables h(t) and z(t-1) is the vector $$z(t-1)=[h(t-1),\ldots,h(t-n),q(t-1),\ldots,q(t-n)]^T$$

Given this formulation a consistent maximum likelihood estimator may be derived. The state and output data is provided to a model 30 to determine whether AHE is occurring, which provides for a predicted start time of AHE at a decision time.

Figure 3:
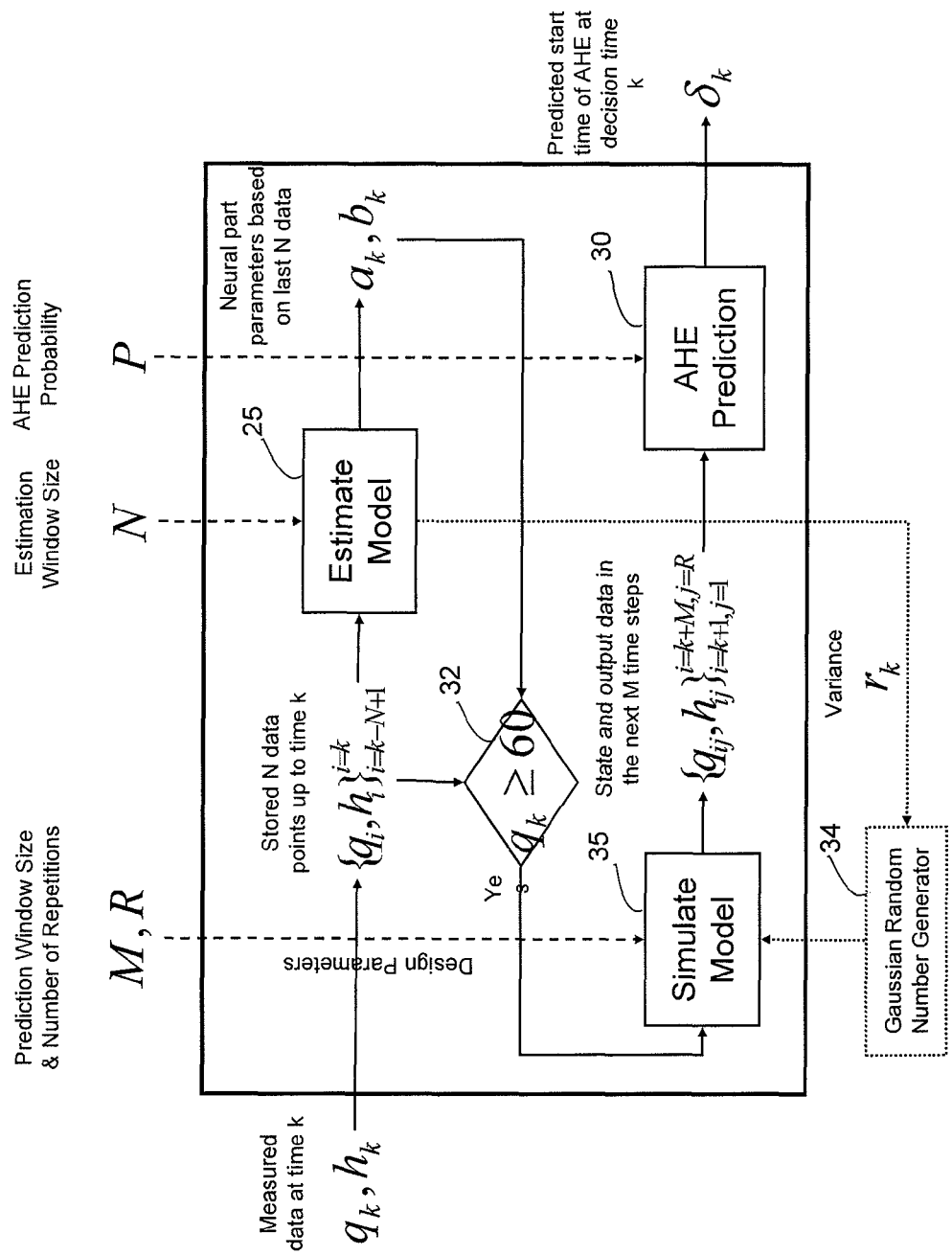
FIG. 3 depicts an exemplary embodiment of a predictive assessment algorithm implementation block diagram.

FIG. 3 depicts an exemplary embodiment of a predictive assessment algorithm implementation block diagram. As further illustrated, determination, at 32, is made whether the MAP is already below a certain level, such as 60 mmHg. This level is selected because AHE has already started and is still the same AHE. As explained above the predict state and output model 27 include a Gaussian random number generator 34 and a simulate model 35, which considers the prediction window size, M, and a number of repetitions, R.

Figure 4:
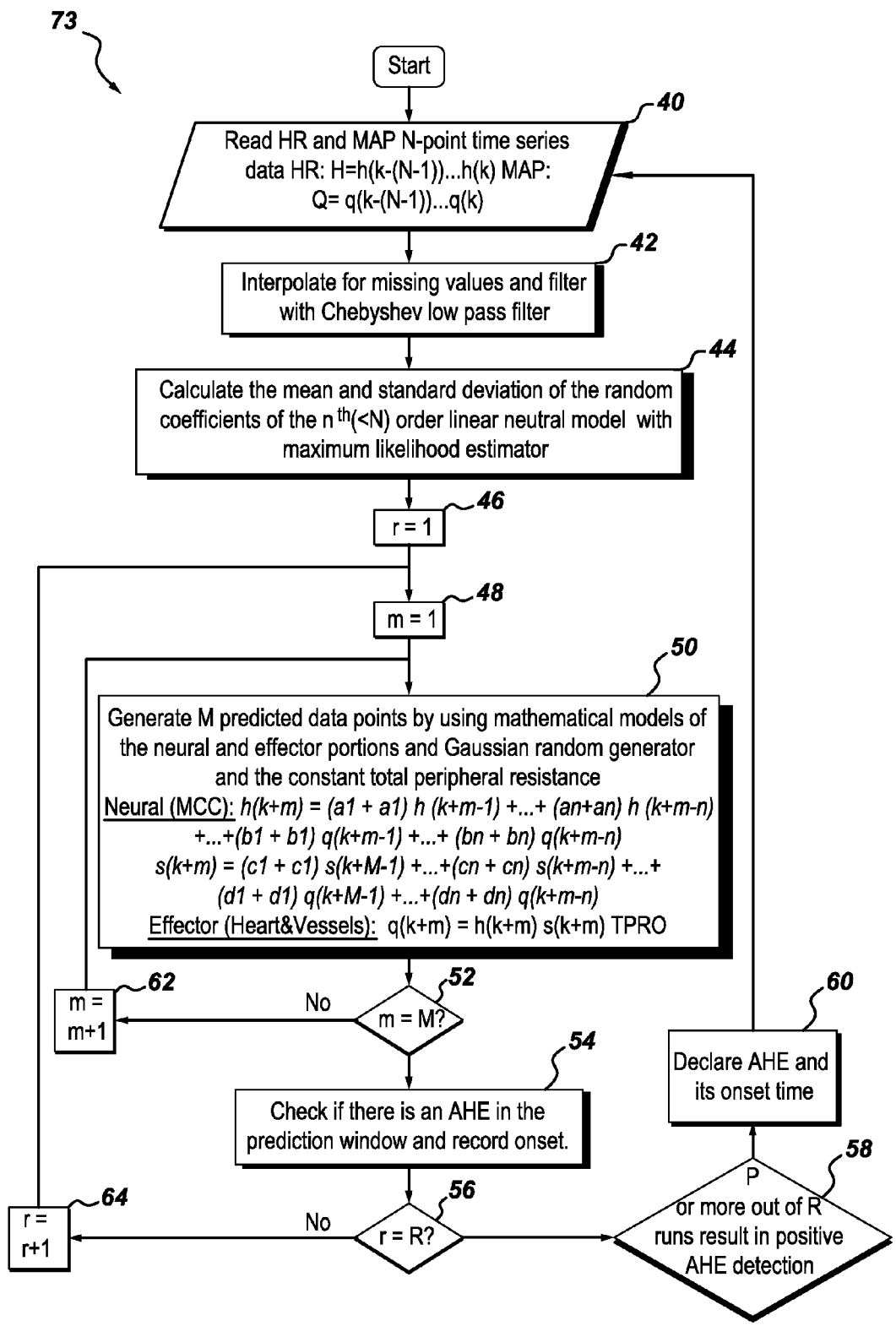
FIG. 4 depicts an exemplary embodiment of a predictive assessment algorithm flow chart.

FIG. 4 depicts an exemplary embodiment of a predictive assessment algorithm flow chart 73. As is illustrated in FIG. 3, and further provided in FIG. 4, predictive assessment design parameters needed to run the predictive assessment algorithm include prediction window size M in time units, number of repetitions, R, of the simulation of the system to predict evolution of cardiovascular variables which is an integer, estimation window size, N, in time units, and probability of occurrence of AHE based on R number of predictions within each run of the predictive assessment algorithm, a real number between zero (0) and one (1).

As illustrated, heart rate data is read from a patient over a given time period (at least thirty minutes), N, and so is MAP data read from the patient patent over the given time period, N, at 40. The heart rate data and MAP data may have the following mathematical formulas:

$$H = h(k-(N-1)) \ldots h(k)$$

and $$Q = q(k-(N-1)) \ldots q(k).$$

Conditioning the heart rate data and the MAP data for use in determining an onset of an acute hypotensive episode is performed, at 42. This may be performed by interpolating for missing values and use of a filter 71, such as but not limited to a Chebyshev low pass filter 71. A mean and standard deviation of random coefficients of the nth (<N) order linear neural portion with a maximum likelihood estimator is calculated, at 44. The value for a loop index for repetition, r, is set to one, at 46. When the value of r reaches R the number of repetitions needed for the rest of the algorithm is completed. The values of m, which is for a loop index to get M data values to run the prediction, is also set to one, at 48. M predicted data points are generated, at 50. They may be generated by using mathematical models of the neural portion, effector portion, a Gaussian random generator, and constant total peripheral resistance based on previous measured data points of heart rate and MAP and approximated data points of stroke volume. For example, the mathematical model for the neural portion may be:

$$h(k+m) = (a1+\alpha1)h(k+m-1) + \ldots + (an+\alpha n)h(k+m-n) + \ldots + (b1+\beta1)q(k+m-1) + \ldots + (bn+\beta n)q(k+m-n)$$

$$s(k+m) = (c1+\chi1)s(k+M-1) + \ldots + (cn+\chi n)s(k+m-n) + \ldots + (d1+\delta1)q(k+m-1) + \ldots + (dn+\delta n)q(k+m-n)$$

and the mathematical model for the effector portion may be:

$$q(k+m) = h(k+m)s(k+m)TPR0$$

where h denotes the heart rate, s denotes the stroke volume, q denotes MAP, TPR0 denotes the total peripheral resistance, n denotes the order of the system, k denotes current discrete time, m denotes the discrete prediction time. The order of the system is greater than or equal to 1 and less than or equal to N, where N is a size of the estimation window. Stroke volume is approximated by using the age of the patient and pulse pressure, i.e., the difference between measured systolic and diastolic arterial pressure. Specifically, stroke volume is calculated as multiplication of the pulse pressure and arterial compliance where arterial compliance is approximated as a linear function of age. The mathematical model for the arterial compliance may be:

$$\text{Arterial Compliance} = (160 - \text{Age})/70,$$

with an assumption that a human age 20 years old has arterial compliance of 2 mL/mmHg.

A determination is made when m equals M, at 52. If they equal, a determination is made as to whether an AHE is within the prediction window and the onset is recorded, at 54. A determination is then made regarding whether r equals R, at 56. It they are equal, a determination is made whether P or more out of R runs result in positive AHE detection, at 58, where P is the AHE prediction threshold and R is the number of repetitions as described in detail above. P is less than or equal to R. If a positive AHE detection is found for P out of R repetitions, an AHE is declared and its onset time is known, at 60.

If m does not equal M, then m is increased by an increment of one, at 62, another prediction data point is generated until m is equal to M and M prediction data points are generated. If r does not equal R, then r is increased by an increment of one, at 64, and the M predicted data points are generated again until r is equal to R and R many M predicted data points are generated.

In operation, at least two or more runs are preferred because the simulate model contains random coefficients. Each simulation run should predict long enough periods that include the decision window and at least one AHE within the prediction window. That simulating a run of the model for only as long as the minimum duration of AHE given estimated parameters, physical model, and initial conditions and check for AHE within that window, it is likely that the onset of the next AHE will happen in a minute and that is not useful to clinicians. Thus, the prediction window should be greater than the summation of N and M. One other check is to test whether the simulated model is stable or not with the random coefficients. If the parameters result in an unstable system, the prediction result should be discarded for that run and the run should be repeated until a stable run is achieved.

In addition, the records, or data collected, contain artifacts that can be cleaned up to some degree with a low pass filter 71. For example, parameters of an exemplary low pass filter 71 are a Chebyschev Type I filter with a ripple of 0.05 and a cut-off frequency of 0.0001, where a sampling rate is ⅟60 Hz. Thus, each record is preprocessed, at some point, before inputting to the predictive assessment algorithm, or model. The Chebyschev type filter is used to remove high frequency noise. A moving average filter may be used to remove Gaussian noise. An interpolation filter may be used to fill in missing data, where an exemplary reason for missing data is hardware malfunction or bits getting lost in a wireless network. Though the filter 71 is illustrated as being placed between the sensors 32 and the estimate model 25, in other exemplary embodiments it may be located at other locations, such as but not limited to before the prediction model 30.

Figure 5:
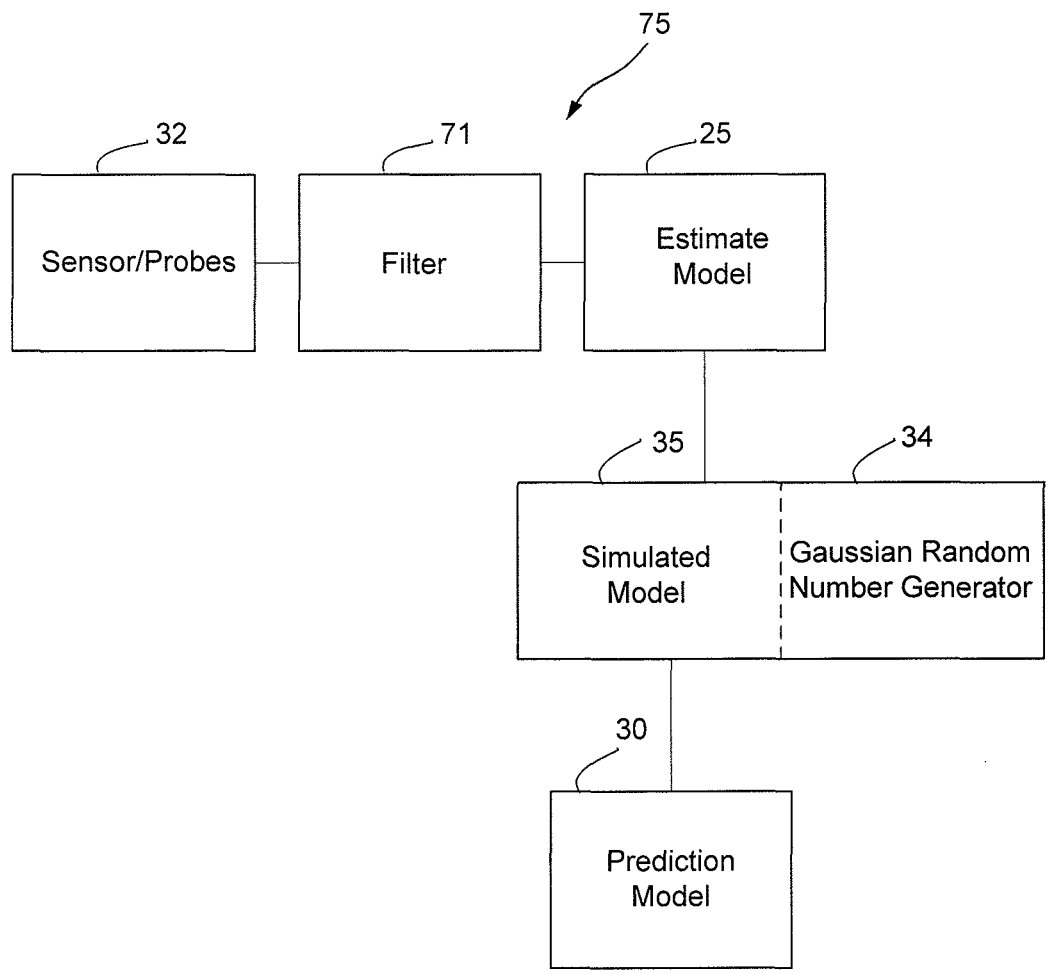
FIG. 5 depicts an exemplary embodiment of a block diagram illustrating elements of a system for predicting an onset of AHE.

FIG. 5 depicts an exemplary embodiment of a block diagram illustrating elements of a system 75 for predicting an onset of AHE. As disclosed above, exemplary embodiments may also be applicable to other conditions described as a pattern in MAP similar to AHE that may be life threatening to patients As illustrated a plurality of sensors 32, collectors, and/or probes, are provided to measure heart rate, MAP, stroke volume, or total peripheral resistance, age, etc., of a patient. Some of the information may be actually measured, but may be calculated and/or approximated based on measured data. For example, when it is not possible to measure stroke volume directly, pulse pressure and age of the patient can be used to approximate the stroke volume. The estimate model 25 is configured to receive data from the sensors 32, collectors, and/or probes. The simulate model 35 is configured to receive information from the estimate model 25 to simulate operation of the effector portion 10 and neural portion 12 of the arterial baroreceptor reflex pathway. The prediction model 30 configured predict onset of an AHE based on results from the simulate model. A Gaussian random number generator is configured to provide random coefficients for the neural portion based on a mean and standard deviation calculated by the estimate model using a maximum likelihood estimator, based on the patient's past read heart rate and MAP to the simulate model.

In operation, the simulate model 35 has a prediction window size of more than thirty minutes. Additionally, the simulate model 35 performs a given number of repetitions before providing information to the prediction model 30. Multiple repetitions are performed because of the stochastic nature of the neural portion since one or more parameters that effect the outcome of the neural portion is not controllable, such as but not limited to ambient temperature or not observable unless high-level monitoring solutions are in place, such as cell and/or molecular level activities. The estimate model 25 is provided a defined size of data collected over at least a thirty-minute period. The period could be longer, where it may be defined by data that is available. A filter 71 may also be provided to clean data collected by the sensors, collectors and/or probes 32 before providing the data to the simulate model 35. The filter 71 may include, but is not limited to a Chebyschev type filter to remove high frequency noise, a moving average filter to remove Gaussian noise, and/or an interpolation filter to fill in missing data, where an exemplary reason for missing data is hardware malfunction or bits getting lost in a wireless network. Each model and Gaussian random number generator 34 may be implemented through algorithms, and/or a computer software code.

While the invention has been described with reference to various exemplary embodiments, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining onset of an acute hypotensive episode, the method comprising:
   determining heart rate and mean arterial pressure of a patient at a given time using one or more sensors coupled to the patient;
   estimating, using at least one processor, an onset of an acute hypotensive episode based on the measured heart rate and mean arterial pressure at the given time in association with heart rate and mean arterial pressure time-series data prior to the given time within a predetermined period;
   simulating, using the processor, an evolution of mean arterial pressure based on a mathematical model of a neural portion of an arterial baroreceptor reflex pathway for a predetermined prediction period and further based on a number of repetitive runs, wherein the neural portion parameters are random coefficients of a linear system described as an nth order differential equation with random coefficients calculated via a maximum likelihood estimator using past read heart rate and mean arterial pressure of the patient over a predetermined estimation period;
   predicting, using the processor, the acute hypotensive episode based on results from simulating the onset of the acute hypotensive episode; and
   reporting, using the processor, the predicted acute hypotensive episode.

2. The method according to claim 1, wherein the predetermined prediction period is at least a minimum length of the acute hypotensive episode defined as thirty minutes.

3. The method according to claim 1, wherein the predetermined estimation period is at most a length of a recorded heart rate and mean arterial pressure data since an initiation of vital sign recording for the patient.

4. The method according to claim 1, wherein an order of the differential equations is greater than or equal to 1 and less than or equal to a pre-determined estimation window.

5. The method according to claim 1, further comprising prohibiting predicting the acute hypotensive episode when the measured mean arterial pressure is below a predetermined level such as 60 mmHg for acute hypotensive episode (AHE) for a predetermined period such as thirty minutes for AHE.

6. The method according to claim 1, wherein predicting the acute hypotensive episode further comprises simulating an evolution of mean arterial pressure using a mathematical model of an effector portion of an arterial baroreceptor reflex pathway.

7. The method according to claim 1, wherein predicting the acute hypotensive episode further comprises simulating an evolution of mean arterial pressure using a Gaussian random generator and constant total peripheral resistance.

8. The method according to claim 1, wherein predicting the acute hypotensive episode further comprising determining whether the acute hypotensive episode has occurred within a prediction window.

9. The method according to claim 1, further comprises filtering data associated with determining heart rate and mean arterial pressure.

10. A non-transitory computer readable medium having computer software code embodied thereon that is configured for execution with a processor designated for collecting and controlling sharing of data associated with a patient's medical condition, the computer software code comprising instructions for performing a method comprising:
    determining heart rate and mean arterial pressure of a patient at a given time using data obtained from one or more sensors;
    estimating an onset of an acute hypotensive episode based on the measured heart rate and mean arterial pressure at the given time in association with heart rate and mean arterial pressure time-series data prior to the given time within a predetermined period;
    simulating an evolution of the measured mean arterial pressure based on a mathematical model of a neural portion of an arterial baroreceptor reflex pathway for a predetermined prediction period and further based on a number of repetitive runs, wherein the neural portion parameters are random coefficients of a linear system described as an nth order differential equation with random coefficients calculated via a maximum likelihood estimator using past read heart rate and mean arterial pressure of the patient over a predetermined estimation period; and
    predicting the acute hypotensive episode based on results from simulating the onset of the acute hypotensive episode; and
    reporting the predicted acute hypotensive episode.

11. The non-transitory computer readable medium according to claim 10, wherein the method further comprises prohibiting predicting the acute hypotensive episode when the mean arterial pressure is above a predetermined level for a predetermined period.

12. The non-transitory computer readable medium according to claim 10, wherein the method further comprises filtering data associated with determining heart rate and mean arterial pressure.

\* \* \* \* \*